(12) United States Patent
Mayer et al.

(10) Patent No.: US 10,507,083 B2
(45) Date of Patent: Dec. 17, 2019

(54) AFFIXING AN ARTIFICIAL ELEMENT TO A SURFACE OF DENTINE, ENAMEL, BONE, OR A CORRESPONDING SUBSTITUTE MATERIAL

(75) Inventors: Jörg Mayer, Niederlenz (CH); Andrea Mueller, Winterthur (CH); Urs Weber, Evilard (CH)

(73) Assignee: WOODWELDING AG, Stansstad (CH)

( * ) Notice: Subject to any disclaimer, the term of this patent is extended or adjusted under 35 U.S.C. 154(b) by 1716 days.

(21) Appl. No.: 13/541,900

(22) Filed: Jul. 5, 2012

(65) Prior Publication Data

US 2013/0004917 A1 Jan. 3, 2013

Related U.S. Application Data

(63) Continuation-in-part of application No. 12/521,217, filed as application No. PCT/CH2007/000620 on Dec. 11, 2007, now Pat. No. 8,226,411.

(60) Provisional application No. 60/882,252, filed on Dec. 28, 2006.

(51) Int. Cl.
- *A61C 8/00* (2006.01)
- *A61C 5/30* (2017.01)
- *A61K 6/02* (2006.01)
- *A61K 6/06* (2006.01)

(Continued)

(52) U.S. Cl.
CPC ............ *A61C 8/0016* (2013.01); *A61C 5/30* (2017.02)

(58) Field of Classification Search
CPC ......... A61C 8/0016; A61C 5/08; A61C 5/002; A61C 13/28; A61B 17/8802; A61K 5/0205; A61K 6/06; A61K 6/08; A61L 24/0094; A61L 2430/02; A61L 2460/12
USPC ...... 433/169, 172–176, 86, 119; 128/200.16; 451/165, 910; 604/22; 606/169, 171, (Continued)

(56) References Cited

U.S. PATENT DOCUMENTS

| | | | |
|---|---|---|---|
| 2,528,219 A | * | 10/1950 | Feagin ............. A61C 13/081 249/54 |
| 3,462,839 A | | 8/1969 | Boyer et al. |
| 4,566,138 A | | 1/1986 | Lewis et al. |

(Continued)

FOREIGN PATENT DOCUMENTS

| | | |
|---|---|---|
| JP | 2000093500 | 4/2000 |
| WO | 99/52478 | 10/1999 |

(Continued)

*Primary Examiner* — Heidi M Eide
*Assistant Examiner* — Mirayda A Aponte
(74) *Attorney, Agent, or Firm* — Rankin, Hill & Clark LLP

(57) ABSTRACT

A medical method of affixing an element to a surface of dentine, tooth enamel, bone tissue, or corresponding substitute material. The method includes the steps of: providing an attachment composition, the attachment composition having a mixture of: a thermoplastic component; and a hardenable (for example curable) component. The hardenable component is different from the thermoplastic component. The method further includes the steps of: positioning the attachment composition relative to the surface of dentine, tooth enamel, bone tissue, or corresponding substitute material; and activating the attachment composition to attach to the surface or to attach to the element positioned relative to the surface. The step of activating the attachment composition includes activating the attachment composition by means of mechanical vibration.

36 Claims, 6 Drawing Sheets

(51) Int. Cl.
*A61K 6/08* (2006.01)
*A61B 17/88* (2006.01)

(58) Field of Classification Search
USPC ......... 606/177, 178; 106/35; 427/2.1, 2.29;
523/118, 116, 120, 319; 522/1, 4, 5, 6
See application file for complete search history.

(56) References Cited

U.S. PATENT DOCUMENTS

| | | |
|---|---|---|
| 4,975,059 A | 12/1990 | Sendax |
| 5,709,548 A | 1/1998 | Oxman et al. |
| 5,746,856 A | 5/1998 | Hendershot et al. |
| 5,773,794 A | 6/1998 | Zimet-Sternberg et al. |
| 5,948,427 A * | 9/1999 | Yamamoto ............ A61L 24/001 424/426 |
| 6,133,339 A | 10/2000 | Xie et al. |
| 6,709,526 B1 | 3/2004 | Bailey et al. |
| 6,955,540 B2 * | 10/2005 | Mayer ..................... A61C 5/00 433/169 |
| 7,435,764 B2 | 10/2008 | Vallittu et al. |
| 2004/0053196 A1 * | 3/2004 | Mayer ..................... A61B 17/68 433/173 |
| 2004/0197311 A1 | 10/2004 | Brekke et al. |
| 2007/0054244 A1 | 3/2007 | Vallittu et al. |

FOREIGN PATENT DOCUMENTS

| | | |
|---|---|---|
| WO | 02/069817 | 9/2002 |
| WO | 2004/017857 | 3/2004 |
| WO | 2004/103319 | 12/2004 |
| WO | 2005/079696 | 9/2005 |
| WO | 2007/092869 | 8/2007 |

* cited by examiner

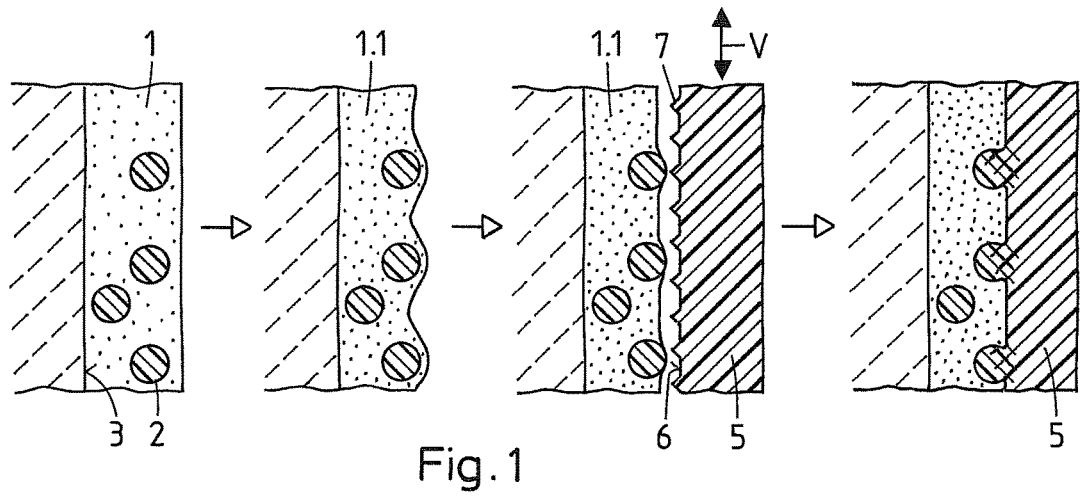
Fig. 1
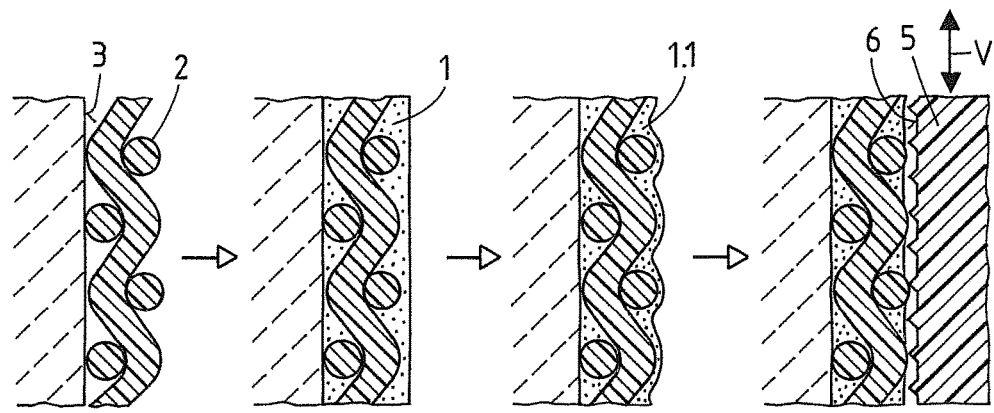
Fig. 2
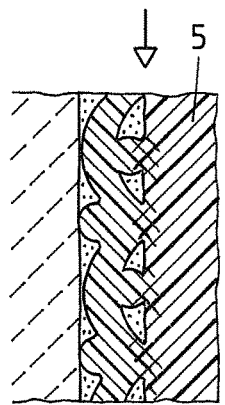

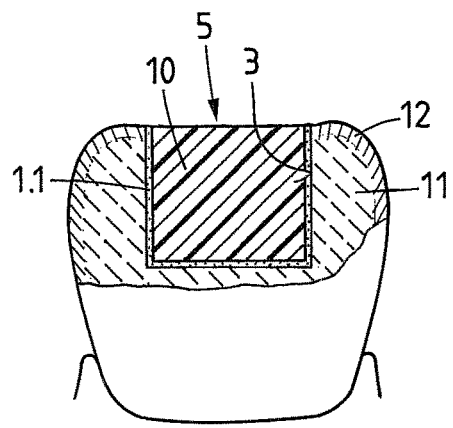
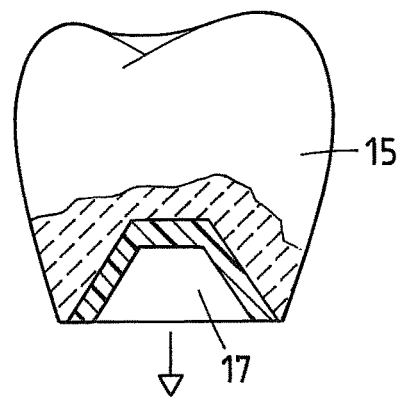
Fig. 3
Fig. 4
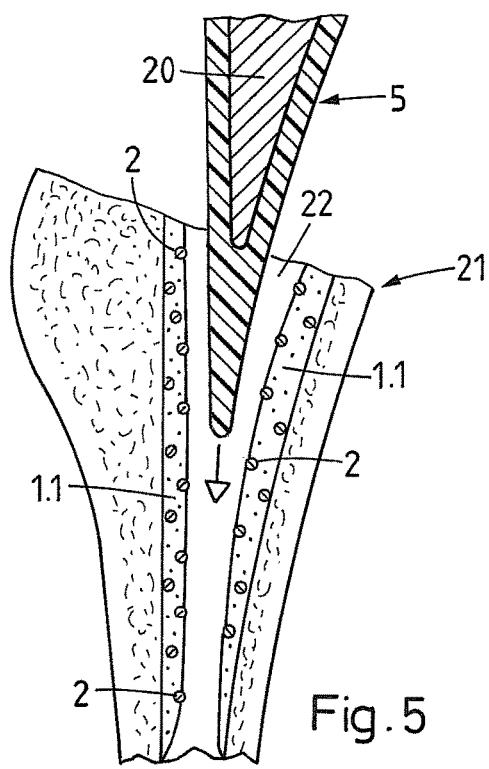
Fig. 5

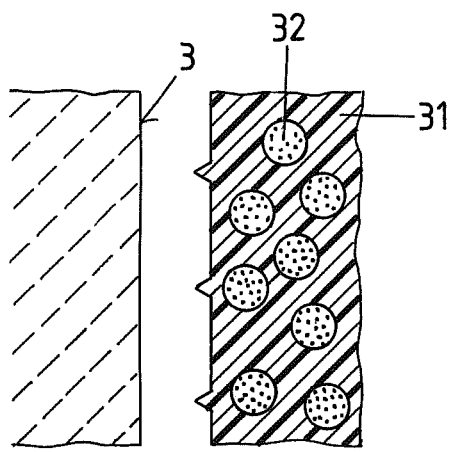 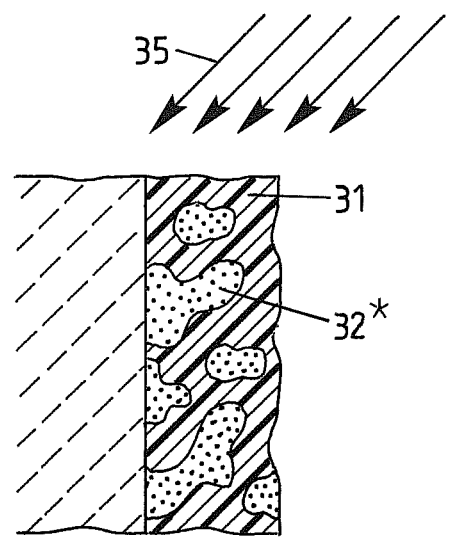
Fig. 9a Fig. 9b
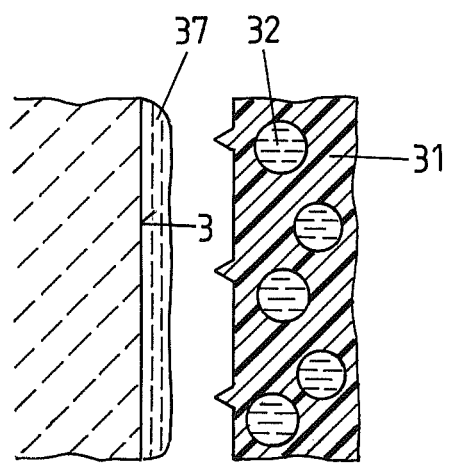 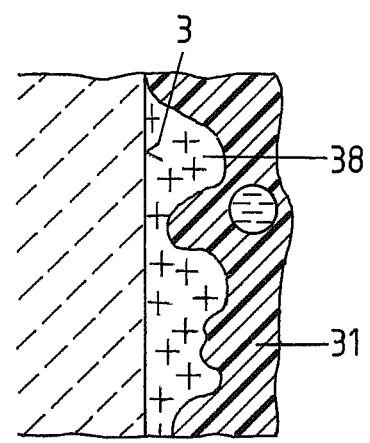
Fig. 10a Fig. 10b

AFFIXING AN ARTIFICIAL ELEMENT TO A SURFACE OF DENTINE, ENAMEL, BONE, OR A CORRESPONDING SUBSTITUTE MATERIAL

This application is a continuation-in-part of U.S. Ser. No. 12/521,217 filed on Aug. 10, 2009 and currently pending. U.S. Ser. No. 12/521,217 is a national stage filing of PCT/CH2007/000620 filed on Dec. 11, 2007 which claims priority to U.S. Provisional Application 60/882,252 filed on Dec. 28, 2006.

BACKGROUND OF THE INVENTION

The invention lies in the field of medical technology and concerns a method, a composition, and a set according for the affixing or fastening of an artificial element to a surface of dentine, tooth enamel, bone tissue, or of a corresponding substitute material.

It is well known in dentistry to make e.g. fillings, inlays, dental veneers, or cement for fixing brackets of dental braces, crowns, inlays or bridges from composite materials. These composite materials usually comprise a curable matrix material and filler materials contained in the matrix material. The composite materials are applied in the form of a paste to the surface where they are to adhere and they are cured in situ. The matrix material is e.g. a polymer which is curable by cross-linking, it is e.g. based on polymethacrylate or polymethylmethacrylate, wherein the in-situ curing is initiated by ultraviolet light. The filler material is e.g. a ceramic material, a glass-ceramic, or a glass, and is contained in the matrix material as e.g. particles, fibers, or whiskers.

In order to achieve an effective bond between the aforementioned composite materials and the dentine or enamel surfaces of the tooth, these surfaces are pre-treated. For this preparatory treatment e.g. etching agents, sealing agents, adhesion promoters and/or adhesion agents are used, which are either applied in succession (e.g. adhesive systems of conditioner, primer, and adhesive) or which are contained within a single primer preparation requiring just one application. One of the purposes of the preparatory treatment is to render the inherently hydrophilic dentine and enamel surfaces receptive to the usually hydrophobic composite material to be adhered to it, to create covalent or ionic bonds with molecules of the dentine or enamel surface, and to provide molecules capable of covalent or ionic bonding between the pre-treated surface and the material to be attached to it. Corresponding molecules and preparations belong to the state-of-the-art technology.

Usually at least one of the pre-treatment preparations comprises a polymer which is curable by cross-linking and/or corresponding monomers or oligomers, wherein this polymer is adapted to the matrix material of the composite material to be affixed to the pretreated surface in such a way that cross-linking between components of the pre-treatment preparation and the matrix material becomes possible.

The aforementioned pre-treatment preparations are usually applied to the dentine or enamel surface in one or several steps of preparatory treatment and, if necessary, partly cured. Then the composite material is applied to the pre-treated dentine or enamel surface and the composite material is cured, wherein not fully cured components of the pre-treatment preparation are completely cured also.

It is also a known practice to affix implants to bones or bone sections, wherein a bone cement is applied between the implant and the bone or bone section. Such cements are also solidifiable (curable) and fulfill similar functions as the aforementioned pre-treatment preparation used in dentistry. The cements can be polymer, ceramic or hydraulic cements and usually also contain filler materials.

Another procedure known e.g. from the publications WO 02/069 817, WO 2004/017 857, and WO 2005/079 696, is to fasten elements, consisting at least in part of thermoplastic material, to surfaces of bone tissue, dentine, or tooth enamel, by pressing the element against said surfaces and exciting it with mechanical vibration, e.g. ultrasonic vibration, so that the thermoplastic material is softened at the contact surfaces and pressed into pores and surface irregularities of the bone tissue, dentine, or enamel, in order to form a form-fit connection after re-solidification. This method has the important advantages that there is no need for a preparatory treatment of the surfaces and that, compared to the method using curable composite materials as briefly mentioned above, causes less or practically no shrinkage.

BRIEF SUMMARY OF THE INVENTION

The object of the invention is to create a further method by which an artificial element can be affixed to a surface of dentine, tooth enamel, bone tissue, or a corresponding substitute material. The fixations created by the method according to the invention are to have similar stabilities as the known fixations as briefly described above. It is a further object of the invention to create a set for carrying out the method.

These objects are achieved by the method and the set as defined in the corresponding independent claims.

In accordance with an aspect of the invention, a medical method of affixing an element to a surface of dentine, tooth enamel, bone tissue, or corresponding substitute material is provided, the method comprising the steps of: Providing an attachment composition, the attachment composition comprising a mixture of:

A thermoplastic component; and

A hardenable (for example curable) component, the hardenable component being different from the thermoplastic component;

Positioning the attachment composition relative to the surface of dentine, tooth enamel, bone tissue, or corresponding substitute material; and Activating the attachment composition for attachment to the surface or for attachment to the element positioned relative to the surface;

Wherein the step of activating the attachment composition comprises activating the attachment composition by means of mechanical vibration.

By the step of activating, the attachment composition is activated to attach to the surface or the element, and/or the attachment composition is brought into a condition in which such attachment becomes possible, for example by an additional curing step.

In this, the attachment composition may, according to a first option, belong to a pre-treatment preparation applied to the surface prior to the positioning of the element relative to the surface. According to a second option, the attachment composition may be a composition of the element (or a portion thereof, which portion forms part of the surface) itself.

A hardening process in this text is a chemical process in which a material is—usually irreversibly—made harder than it was before. Especially, hardening may be a full or partial curing, e.g. by cross-linking, but other chemical reactions leading to a harder end state are not excluded. A hardenable material is a material that can be made harder in situ (i.e. applied to the surface of dentine, tooth enamel, bone tissue, or corresponding substitute material) by a hardening process; this excludes materials that can only get harder in a purely physical, reversible process for example by merely reversibly being cooled down.

A principle of the method is based on the combination of a thermoplastic material with the activation by mechanical vibration. Especially, the thermoplastic material may—and in most cases will—absorb mechanical energy and be heated thereby. Thus, the mechanical vibration may cause a partial or full liquefaction of the thermoplastic material.

Especially, in an aspect of the invention, one of the components of the attachment composition is activated by the liquefaction due to the mechanical stimulation. For example, one of the components is embedded in the other one and is activated by the liquefaction.

This may be made for example in the following way:

In a welding processes, for example if the attachment composition is separate from the element, and the element itself comprises a thermoplastic material (of a same or different polymer/polymer composition) capable of being welded together with the thermoplastic material of the attachment composition;

Discharging of a material embedded in the thermoplastic matrix that is liquefied by the activation. For example, The hardenable (for example curable) material or at least a part thereof may move to the interface with the substrate (dentine, tooth enamel, bone tissue, substitute material) when the thermoplastic material in which it is embedded melts. In this, the curable material may be liquid or pasty at room temperature before the activation sets in. In addition or as an alternative, it is also possible that the curable material itself has thermoplastic or viscoelastic or thixotropic properties, i.e. have temperature- and/or shear strain dependent properties. For example it may be a high-molecular prepolymer or a prepolymer with partially cristallizeable zones. By the activation, the curable material then is liquefied (or, more in general, its viscosity is reduced) by the activation. This may facilitate wetting of the interface by the curable material, while the material gets sticky and thus sticks well to the surface after the activation process.

In embodiments where the activation comprises discharging in the form of a transport to the interface, curing may be done during the activation (for example due to the effect of the heat generated), and/or thereafter, for example by irradiation, induction, letting time pass, etc.

the attachment composition may comprise the hardenable component in the form of a hardener that initiates a curing process in an initially applied curable material of a pre-treatment preparation, and the hardener at least in part moves to the interface upon activation by the mechanical energy—or vice versa.

the attachment composition may comprise an external mixture of two constituents that harden when brought together. An "external mixture" in this text is something that comprises separate portions of the consitutents, for example particles or droplets of one constitutent and particles or droplets of the other constituent; in an "internal mixture", in contrast, the portions themselves comprise a mix of at least two constituents.

Activating a curing process by the heat generated for liquefaction;

Variants and/or combinations.

The mechanical vibration, in addition to liquefying at least parts of the thermoplastic materials also cause mechanical movement and mechanical treatment of portions (such as particles/droplets) of the embedded component, making possible material transport, mixing, acceleration of chemical processes etc.

In embodiments in which the hardenable (for example curable) component after the process adheres to the surface of dentine, tooth enamel, bone tissue, or corresponding substitute material, this surface may undergo an additional treatment.

For example if the surface is of dentine and/or enamel, the the three steps of:

etching the surface to make it coarse and to remove potential debris such as a smear layer;

bringing the surface in contact with a primer to modify the surface chemistry (for example silanizing);

causing the curable component to adhere to the surface wherein, for example by the curing, a chemical reaction between molecules of the—primed—surface with the curable component occurs.

These three steps can—as known in the art—be carried out separately or be combined to yield a one-step or two-step process. For example, there exist curable materials for dental applications that comprise the primer. Further, there exist curable materials for dental applications that additionally comprise both, the primer and the etchant. Such material compositions with combined functionality are useable in methods according to the invention, too. For example, vesicles of the curable material may comprise an according internal mixture. It would further be possible to provide such material combinations in an external mixture, i.e. for example provide the primer and/or the etchant in separate vesicles within the thermoplastic matrix.

Due to this approach of a combination of a thermoplastic material with the activation by mechanical vibration, a connection between, in principle, not compatible material groups becomes possible.

Also, due to the thermoplastic component/phase, the attachment may become reversible. The attached element may be removed after energy again impinges on the arrangement and re-liquefies the thermoplastic component to release the connection.

In the step of activating, preferably, mechanical vibration having a frequency of between 2 and 200 kHz is applied to the element. Also, in an (optional) step of removing the element, mechanical vibration in this frequency range may be applied. Alternatively other energy sources may be used for removal, for example irradiation, induction or heat transport.

The mechanical vibration—that may be ultrasonic vibration—is for example applied to the element positioned relative to the surface and pressed against the surface either actively—by the operator pressing—or by being locked or the like. The mechanical vibration together with the pressing force may generate friction at the interface, and this may cause the generation of heat—similar to an ultrasonic welding process.

In a first group of embodiments, the element to be affixed to the surface of dentine, tooth enamel, bone tissue, or a corresponding substitute material, at least in the areas of its surface where the fixation is to be achieved, is at least partly made of a first thermoplastic material. In these embodiments, a pre-treatment of the surfaces of dentine, tooth enamel, bone tissue, or a corresponding substitute material, can be achieved by using a generally known or functionally similar pre-treatment preparation comprising at least one curable component in combination with solid bodies comprising a (second) thermoplastic material, wherein the solid bodies are attached to said surfaces essentially by means of the curable components of the preparation. The solid bodies are e.g. particles, fibers, or constitute a flat—possibly three-dimensional—item and they consist entirely of the second thermoplastic material, comprise in addition to the second thermoplastic material a filler, or are coated with the second thermoplastic material. For the preparatory treatment the solid bodies comprising the second thermoplastic material are either already blended with other components of the pre-treatment preparation and/or they are contacted with these in situ. Where the surface to be pre-treated is a substitute material, it is also possible to perform the preparatory treatment ex situ and to connect the pre-treated substitute material with a further element in situ by means of mechanical vibration.

In these embodiments, the pre-treatment preparation comprises the attachment composition and is applied to the relevant surfaces prior to the positioning of the element to be affixed thereto and prior to the welding process, and it is cured to such an extent that the solid bodies comprising the second thermoplastic material adhere firmly to the surface of dentine, tooth enamel, bone tissue, or the corresponding substitute material. Curing of the pre-treatment preparation before welding may be a complete curing or possibly a partial curing only, with completion of the curing to be effected during or after the welding process.

The pre-treatment preparation being modified according to these embodiments has a function regarding the surface of dentine, tooth enamel, bone tissue, or the corresponding substitute material, which is substantially the same as the function of per se known pre-treatment preparations as briefly described further above. With regard to the element to be attached, the connecting function is taken over substantially fully by the solid bodies comprising the second thermoplastic material. Other than the generally known such preparations, the pre-treatment preparation of the invention may contain additional molecules, which during the curing process cause e.g. covalent bonds between the cured matrix material and the solid bodies comprising the second thermoplastic material. The expert is familiar with such molecules. They are advantageously provided on the solid bodies.

For instance, for affixing an element of polyamide, solid bodies of polyamide are provided in the pre-treatment preparation while the matrix material is a two-component epoxy system. To enable the polyamide solid bodies to be bound firmly into the matrix material when the epoxy resin is cured, the bodies are e.g. silanized prior to being introduced into the matrix material.

When selecting size and quantity of solid bodies comprising the second thermoplastic material, care needs to be taken that they are available on the pre-treated surfaces in sufficient numbers and with sufficient sizes and that they are sufficiently accessible for being able to be reliably welded. This can be achieved e.g. if the smallest dimensions of the solid bodies are greater than the thickness of a layer to be formed by the other components of the pre-treatment preparation. Experiments further show that the smallest dimensions of the solid bodies comprising the second thermoplastic material are to be at least 2 µm, advantageously 20 µm. It appears that smaller solid bodies produce inferior welded connections, which may be due to the solid bodies being torn from the pre-treated surface by the mechanical vibration used for welding or not being able to be softened or melted by this vibration. Experiments also show that a cured layer of the other components of the pre-treatment preparation which layer covers the solid bodies, i.e. extends between the second thermoplastic material of the solid bodies and the first thermoplastic material of the element to be affixed, does not have any negative effects upon the welding process. This seems to be due to such a layer simply being scraped off, broken up, or removed in some other way, prior to the actual welding, and the debris of the layer being integrated in the molten phase without negative effect on the weld which is achieved.

For achieving a sufficiently stable connection between the pretreated surface and the element of e.g. 10 to 15 N/mm2 at a weld stability of 50-100 N/mm2 it is necessary for the particles to constitute 10 to 20% of the pretreated surface. From such calculation and a known size of the solid bodies and a known thickness of the pretreatment layer, the number of solid bodies to be provided per volume of pretreatment preparation can be estimated.

The second thermoplastic material of the solid bodies of the pre-treatment preparation and the first thermoplastic material of the element to be affixed are matched in such a manner that they are capable of being welded together. As the expert in the field of bonding plastic materials by means of ultrasound or friction is well aware, this implies that both thermoplastic materials have similar melting temperatures and similar viscosities when liquefied and that they are capable of mutual wetting and/or mixing. Advantageously, they both belong to the same class of thermoplastics or are indeed the same thermoplastic. An example of different thermoplastics being capable of being welded together are polycarbonate and polymethylmethacrylate. Other pairings of two different but weldable thermoplastic materials are disclosed e.g. in "Plastics and Composites Welding Handbook, Eds David A. Grewell, Avraham Benatar, Joon B. Park; Hanser Munich, 2003 pp 177-179.

Pairs of thermoplastic materials are weldable through compatibility, i.e. they form one mixed molten phase, or through blending, i.e. the two materials remain separate in the molten phase but mechanically intermingled, wherein the intermingling is enhanced through high shearing forces during the welding process and similar viscosities of the two molten materials. The lower the compatibility of the two materials are, the more it becomes necessary for weldability that the molecular weights of the two materials are such adapted to each other that the two materials have similar shearing viscosities at similar temperatures.

Examples of pairs of thermoplastic materials which are suitable for being used in connection with embodiments of the invention are the following (advantageously of two different materials the first named material is used for the element and the second named material for the solid particles):
polyether ketone and polyether imide (compatible)
polycarbonate and acryl-butadiene-styrene (compatible)
polyamide 12 and polyamide 11 (compatible)
Polyamide 6, 6/6, or 6/4 and any one of polyamide 6, 6/6, or 6/4 (compatible)
Polyether imide and polycarbonate (blending)
Polysulfone and polycarbonate (blending)
Polycarbonate and ABS, polyacrylene, polyether imide, or polysulfone (blending)
polyamide12 or 11 and polyamide 6, 6/6 or 6/4 (blending)
PVC rigid and ABS (blending)

In a further, second group of embodiments, the activatable component is the hardenable component, and it is embedded in the thermoplastic component. In this further group of embodiments, the attachment composition may be of a separate, pre-treatment preparation, or it may belong to the element itself, by forming the element material or for example forming a portion of the element material that interfaces with the dentine, tooth enamel, bone tissue, or corresponding substitute material.

In a sub-group of the second group, the hardenable component may be embedded in the thermoplastic matrix on a molecular scale, for example in blends with oligopolymers that are induced thermomechanically and react at the interface to the surface (e.g. with the collagenous components in dentine, enamel or bone, . . . ).

In a further sub-group, the hardenable component is embedded in the thermoplastic matrix vesicularly (in the form of vesicles). This may be as mono- or prepolymer or an other constituent of a curing composition, for example a chemical additive, or similar. By the liquefaction of the thermoplastic matrix and the mechanical shear, the vesicles are broken open, and the material can flow to the surface. The hardenable component will often not be mixable or mixable only to a limited extent with the thermoplastic matrix; hence the vesicles will tend to flow to the surface, where the material can make a connection with the surface by a chemical setting reaction. To this end, the surface may have been pre-treated prior to the positioning of the element, so that the surface is etched and/or primed, and/or so that the surface comprises a pre-treatment preparation.

Therein, several constituents of the hardenable component can be embedded, and/or other components can be embedded, for example an etchant, a primer, a starter, a netting adhesive polymer, a compatibilizer between the thermoplastic component and the reactant. Alternatively, such other components, for example for pre-treatment, can be embedded in separate vesicles, as mentioned hereinbefore.

Material compositions for embodiments of the second group may be from material systems that have been known from adhesive systems for cementing restoration. Techniques for integrating liquids in the form of microvesicles or of particles in a matrix have been known from drug release systems or from food processing; they include solvent based techniques, mechanical treatment, sintering etc. The microvesicles themselves can be protected by encapsulation techniques e.g. for drug encapsulation lie reactive phase inversion etc. According to an alternative, the curable component can itself have thermoplastic, viscoelastic or thixotropic properties and be solid or highly viscous at room temperature. In these embodiments, the curable component can be admixed to the thermoplastic component in powder form. Liquefaction then occurs only during activation by the mechanical vibration.

In yet another sub-group of the second group, the first and second components are both contained in a carrier liquid. Such a carrier liquid may be a solvent and/or a slurring agent. For example, both components can be present as particles in the liquid, or one component can be dissolved and the other one can be present as particles, or both can be dissolved. Due to the presence of the carrier liquid, the attachment composition may be pasty and sticky and can be applied with a tool (brush applicator or the like) the dentist knows for other applications, such as application of cavity linings, sealants etc.

In this sub-group, the carrier liquid can be removed—for example by evaporation—before, during, and/or after the activation step. During the application step, particles of the thermoplastic component are welded together. Also the curable component can optionally have thermoplastic, viscoelastic or thixotropic properties and become more flowable by the activation process so that the surface is even better coated by the curable component due to the flowability of the latter.

An example of a suitable carrier liquid is an alcohol, such as ethanol.

Examples of elements which can be advantageously attached to surfaces of dentine, tooth enamel, or corresponding substitute materials (e.g. ceramic materials of dental implants such as zirconiumoxide or ceramics based on calcium phosphate) using the method according to the invention, are fillings to be fixed in tooth cavities, dental veneers or inlays to be fastened on appropriately prepared teeth, crowns, bridges, or partial prostheses to be mounted on tooth stumps, fittings (such as brackets) for dental corrections or jewellery to be fastened to teeth, or root pins to be secured in dental roots.

Examples of elements, which can be advantageously attached to surfaces of bone tissue or corresponding substitute materials (e.g. bone replacement materials based on calcium phosphate) with the method according to the invention, are implants (e.g. dental implants), endoprostheses, or therapeutic elements e.g. equipped to release a therapeutic agent.

Said elements may consist entirely of a (the first, for example) thermoplastic material, wherein this material may further comprise filler materials in varying concentrations. Alternatively, thermoplastic material may only be provided on those surface areas of the element, which are to come into contact with the pre-treated surfaces, while other areas consist e.g. of metal, ceramics, or glass.

Thermoplastic materials suitable on the one hand for elements to be fastened to surfaces of dentine, tooth enamel, bone tissue, or corresponding substitute materials, and on the other hand for the solid bodies of the corresponding pre-treatment preparation, may or may not be resorbable, depending on the application. Resorbable materials are e.g. polymers based on lactic and/or glycolic acid (PLA, PLLA, PGA, PLGA, etc.), polyhydroxy alkanoates (PHA), polycaprolactone (PCL), polysaccharides, polydioxanons (PD), polyanhydrides, polypeptides, or corresponding copolymers or mixed polymers. Non-resorbable polymers are e.g. polyolefins, polyacrylates, polymethacrylates, polycarbonates, polyamides, polyesters, polyurethanes, polysulphones, polyarylketones, polyetherketones, polyetherimides, polyamides, acryl-butadiene-styrene, polyphenylsulphides, liquid-crystal polymers (LCP), polyacetales, halogenated polymers (in particular halogenated polyolefins, polyphenylsulphides, polysulphones), polyether, PVC, ABS or corresponding copolymers and mixed polymers. As already mentioned above, these materials can also be used in a filled state (composite materials) in the element to be affixed and/or in the solid bodies of the pre-treatment preparation.

A further group of thermoplastic materials, especially suitable for temporary fixation, for example of dental crowns, are meltable organic material of relatively low molecular weight such as waxes, low-molecular polylefines, paraffines etc. These materials will make a release with minimal energy input possible and are thus especially suited for applications in which they are to hold for a limited time only and are to bear only limited loads. Further such materials are organic binders that are used in powder injection molding.

These materials suitable for temporary fixation may be provided with fillers known for dental cements, for example metal oxide or silicate fillers.

The invention also concerns an attachment composition for affixing an element to a surface of dentine, tooth enamel, bone tissue, or corresponding substitute material The attachment composition may be a composition that can be used to shape an element to be affixed, or to form a pre-treatment preparation—or both. A set further comprises information on the use of mechanical vibration for the affixation. It may in addition contain information on preparation steps, pre-treatment preparations to be used in combination with the element on what kind of element is to be used in combination with the attachment composition (if the latter is not part of the element), etc.

BRIEF DESCRIPTION OF THE DRAWINGS

The principle of the method according to the invention and exemplary applications thereof are described in detail in connection with the following Figs., wherein:

FIG. 1 shows the principle of an exemplary embodiment of the method according to the invention, wherein the solid bodies comprising the second thermoplastic material are used in conjunction with at least a part of the further components of the pre-treatment compound;

FIG. 2 shows the principle of an exemplary embodiment of the method according to the invention, wherein the solid bodies comprising the second thermoplastic material are united with the further components of the pre-treatment preparation in situ;

FIG. 3 shows an application of the method according to the invention;

FIG. 4 shows another application of the method according to the invention;

FIG. 5 shows an even further application of the method according to the invention;

FIG. 9a shows the principle of a further embodiment of the invention during a first stage;

FIG. 9b shows the embodiment of FIG. 9a during a second stage;

FIG. 10a depicts the principle of yet a further embodiment of the invention during a first stage;

FIG. 10b shows the embodiment of FIG. 9a during a second stage;

DETAILED DESCRIPTION OF THE INVENTION

Figure 6A:
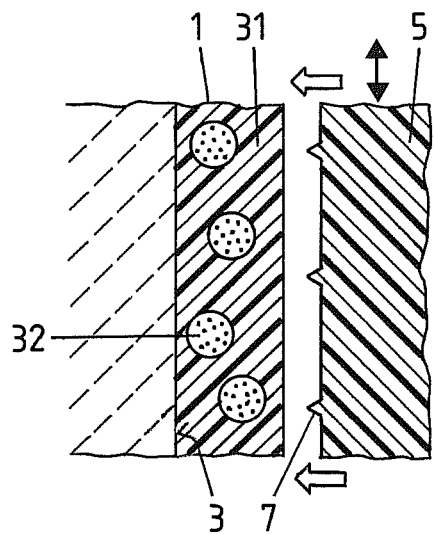
FIG. 6a shows the principle of an embodiment of the invention during a first stage.

FIG. 1 shows a first exemplary embodiment of the method according to the first group of embodiments. The method consists essentially of applying the liquid or paste-like pre-treatment preparation 1—containing a curable component and the solid bodies 2 (in this case particles) comprising the second thermoplastic material—to the surface 3 of dentine, tooth enamel, bone tissue, or the corresponding substitute material, of sufficiently curing the curable component of the pre-treatment preparation 1 by suitable means (e.g. UV light, heat, time), of bringing the element 5 to be affixed into contact with the pre-treated surface, i.e. the surface of the cured pre-treatment preparation 1.1, and of vibrating, which results in the connection between the cured pre-treatment preparation 1.1 and the element 5, as illustrated schematically on the far right in FIG. 1. This connection is based on a welded connection between the first thermoplastic material of the element 5 and the second thermoplastic material of the solid bodies 2 embedded in the cured pre-treatment preparation 1.1.

Instead of generating the heat necessary for melting and welding together the first and second thermoplastic material, it is possible to, instead of vibrating the element and therewith create friction between the element and the surface to which it is to be welded, to position the element in a heated (e.g. molten) state against the surface or to provide radiation (e.g. light) absorbing fillers in one or both of the thermoplastic materials and heat the welding location by corresponding irradiation. It is possible also to heat the material comprising a suitable filler by induction heating.

During application and/or curing, a corresponding and generally known chemistry of the pre-treatment preparation causes reactions with molecules of the surface 3, which result in a firm adhesion between said surface 3 and the cured pre-treatment compound 1.1. The solid bodies 2 comprising the second thermoplastic material are possibly held only mechanically in the at least partially cured pre-treatment preparation 1.1. But it is also possible to additionally equip the pre-treatment preparation and/or the solid bodies to provoke reactions (e.g. cross-linking reactions) with the surfaces of the solid bodies during curing, binding the solid bodies covalently or ionically to other components of the pre-treatment preparation, in particular to the curable component thereof.

Of course, it is possible that the pre-treatment preparation, as is the case with known such preparations, consists of a plurality of components to be applied to said surfaces in succession or to be mixed immediately before application. In such a case, the solid bodies comprising the second thermoplastic material are advantageously added to one of the components, or a mixture of a part of the components, or are mixed therewith immediately before the preparatory treatment.

The element surface 6 to be brought into contact with the pre-treated surface consists at least partly of the first thermoplastic material and, for friction or ultrasonic welding advantageously comprises energy directors 7 in the shape of e.g. ribs or humps. When this surface 6 is in close contact with the pre-treated surface, i.e. the cured pre-treatment preparation 1.1, and the element 5 is vibrated (twin arrow V) by means of a suitable tool (e.g. sonotrode of an ultrasonic device), the two thermoplastic materials are fused together. Any thin layer of non-thermoplastic components of the cured pre-treatment preparation 1.1 is obviously scraped off, broken up, or removed in some other manner from the solid bodies 2 beforehand and therefore do not appear to impede the welding in any way.

If the pre-treatment preparation is a correspondingly modified bone cement, the layer of cured pre-treatment compound 1.1 may be able to level out rough areas of an osseous surface but, as it is cured prior to the positioning of the element to be fastened, it cannot compensate for any irregularities in the element surfaces 6. This is not necessary, however, as such irregularities are automatically cancelled out during the welding process when the surface material of the element 5 is at least partly liquefied.

The set for carrying out the method according to FIG. 1 comprises e.g. the element 5, and of the pre-treatment preparation only the solid bodies 2 comprising the second thermoplastic material. Information concerning further components of the pre-treatment preparation, which are e.g. commercially available and familiar to the expert, as well as guidance with regard to the ratio in which the solid bodies are to be admixed to which components of such preparation, are further enclosed. It is also possible for the set to comprise all components of the pre-treatment preparation, wherein the solid bodies are admixed to at least one component of the preparation or are packaged separately, and wherein the other components of the pre-treatment preparation are already mixed together or are provided in part-mixtures for a successive application and/or for mixing immediately before application.

If applicable the set also contains a tool (e.g. sonotrode for an ultrasonic device) adapted to the element 5, which is suitable for impinging the element 5 with mechanical vibration.

FIG. 2 shows a second exemplary embodiment of the method according to the invention. This method differs from the embodiment according to FIG. 1 in particular in the shape of the solid bodies comprising the second thermoplastic material. This specific form of solid bodies allows for them to be used separately from the other components of the pre-treatment preparation, i.e. to be brought into contact with the other components of the pre-treatment preparation in situ.

The solid bodies 2 comprising the second thermoplastic material are in the method according to FIG. 2 combined to form a flat, e.g. textile item, e.g. a woven item as illustrated. The flat item may also be e.g. a fleece or a perforated sheeting. This flat item is positioned on the surface 3 of dentine, tooth enamel, bone tissue, or a corresponding substitute material and if necessary temporarily fastened by suitable means (e.g. adhesive points, small implants e.g. similar to staples). Before or after positioning the flat item, further components of the pre-treatment preparation are also applied, wherein—particularly in the case of subsequent application—care is to be taken that these further components reach the surface 3 of dentine, tooth enamel, bone tissue, or a corresponding substitute material, through the flat item.

The yarn comprised in the textile item is e.g. a monofilament having a thickness of 10 to 100 µm or it comprises a plurality of filaments. The mesh size is between 10 and 500 µm, wherein on the one hand a sufficient density of welding points is to be achieved, and on the other hand the textile item may have to be penetrable by further components of the pretreatment preparation.

When all components of the pre-treatment preparation are applied, the method is completed as described in connection with FIG. 1. As shown on the far right of FIG. 2, the welding process may lead, in addition to a welding between solid bodies 2 and element surfaces 6, to a further welding between individual solid bodies 2, e.g. between threads or filaments of a weave or fleece.

Of course it is also possible to impregnate the flat item comprising the solid bodies with the other components of the pre-treatment preparation, or with at least a part thereof, prior to its positioning and to store and apply it in this impregnated form.

In the method as illustrated in FIG. 2, the flat item of the solid bodies comprising the second thermoplastic material consists e.g. of filaments (as illustrated), which in turn consist entirely of the second thermoplastic material. However, it is also conceivable that such filaments comprise a core of a different material (e.g. metal, ceramics, carbon fiber, etc.) which is coated with the second thermoplastic material. Thus, the flat item gains a stability, which allows for it to take over additional functions. It is e.g. possible to reinforce, or even partly replace, the walls of a tooth rendered rather thin by drilling.

In the same manner it is possible to construct three-dimensional structures from several layers of the flat item described above and further components of the pre-treatment preparation, particularly the curable components thereof and to render them rigid through curing in situ, and then to fasten the element by welding on this structure. An example of such a three-dimensional structure is a bridge-like bearing structure extending from one prepared tooth across a gap to another prepared tooth, on which, after curing, a dental veneer is attached by mechanical vibration.

The set for carrying out the method as illustrated in FIG. 2 contains e.g. just the flat item (solid bodies 2 comprising the second thermoplastic material) and information regarding further, per se known and e.g. commercially available components for the pre-treatment preparation, regarding elements which are capable to be affixed using the flat item, in particular with regard to the first thermoplastic material, and regarding the use of vibration for the affixation. The flat item is provided to dentists and surgeons e.g. in the shape of a tape, wherein a suitable length is severed from the tape and used depending on the application.

Here too, as described above in connection with the method as illustrated in FIG. 1, it is possible that the set also contains the element to be affixed and/or further components of the pre-treatment preparation and a tool adapted to the element. Therein, the components of the pre-treatment preparation consist e.g. of a generally known primer system or primer compound or a generally known cement, which here too, can consist of two or more components to be mixed immediately before application or to be applied in succession. The flat item comprised in the set may also be impregnated with at least one other component of the pre-treatment preparation.

FIG. 3 shows an exemplary use of the method and set according to the invention. The element 5 to be affixed is a dental filling 10, which is to be fixed to surfaces 3 of dentine 11 and/or enamel 12 in a corresponding cavity. The tooth with the cavity and the element 5 placed in the cavity are shown in cross-section. Also shown, although exaggerated in its thickness, is the layer between the surface 3 and the filling 10, which comprises the cured pre-treatment compound 1.1.

The corresponding set contains e.g. the dental filling 10 comprising the first thermoplastic material, or possibly the material for the construction thereof, and the pre-treatment preparation, wherein the pre-treatment preparation may comprise one or more separate components and wherein the solid bodies are mixed with one of the components or are also provided separately.

FIG. 4 shows another exemplary use of the method and set according to the invention. The element 5 to be affixed is a dental crown 15, which is to be mounted on a stump 16 or on a correspondingly designed dental implant of e.g.

zirconium oxide. Crown 15 and stump 16 are shown in cross-section. The cavity 17 of the crown 15 fitting over the stump 16 of the tooth or implant is coated with the first thermoplastic material or a composite material containing the first thermoplastic material. The stump 16 is treated with the pre-treatment preparation 1 in the manner described above.

A corresponding set contains e.g. the crown 15 and the pre-treatment preparation, which e.g. already contains the solid bodies comprising the second thermoplastic material in the form of particles. The set advantageously also comprises a tool adapted to the crown 15.

If the stump 16, which is to accommodate the crown, is the coronal end of an implant of e.g. zirconium oxide, this implant may also be comprised in the set.

If the stump 16, which is to accommodate the crown, is part of a dental implant, it is also possible to equip the stump with the first thermoplastic material and to carry out the pre-treatment step of the method according to the invention in the cavity of the crown. In such a case, it is possible to perform this preparatory treatment ex situ. However, the assembly of the two parts by welding, of which, in this case, the implant is in the sense of the invention the element to be affixed and the crown the substitute material, is always performed in situ.

FIG. 5 shows another exemplary use of method and set according to the invention. The element 5 to be affixed is the shaft 20 of a hip-joint prosthesis to be secured in an appropriately prepared thighbone 21. Shaft and femur are only partially shown in cross-section. The preparation of the femur 21 in essence comprises the steps of preparing the cavity 22 for the prosthesis shaft 20 and providing in this cavity a cured layer 1.1 of a known cement, wherein the cement has been modified with particles or thread-like items (solid bodies 2) comprising the second thermoplastic material (method according to FIG. 1) or wherein the cement is used in conjunction with a flat item (solid bodies 2) comprising the second thermoplastic material (method according to FIG. 2). The shaft 20 comprises e.g. a metallic core e.g. of a cobalt-chrome alloy and is at least partially coated with the first thermoplastic material or a composite material containing the first thermoplastic material.

Figure 6B:
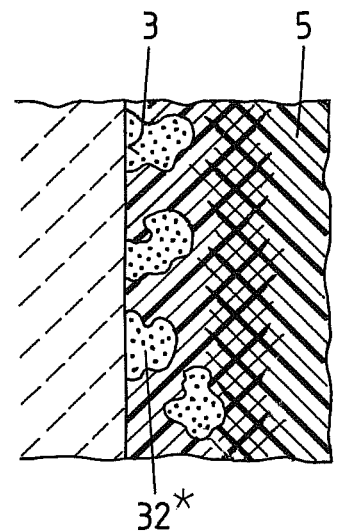
FIG. 6b shows the embodiment of FIG. 6a during a second stage.

FIGS. 6*a* and 6*b* show an example of an embodiment of the second group of embodiments. FIG. 6*a* shows the system before the element is brought into contact with the pre-treatment preparation, and FIG. 6*b* shows the system at the end of the process. The attachment composition again belongs to a pre-treatment preparation 1 that is applied to the surface 3. In this, the thermoplastic matrix 31 may be such as to not adhere to the surface 3 (but to just line it, for example the pre-treatment preparation may be provided as a thin foil placed on the surface) or to stick only weakly—or also strongly—to it; the requirement is only that it is placeable on the surface 3. In addition to the thermoplastic matrix, the pre-treatment composition comprises a hardenable—in embodiments curable—phase, here in the form of vesicles 32 3-dimensionally embedded in the thermoplastic matrix 31. (in an alternative embodiment, the curable component may be molecularly embedded)

When the element 5 to be affixed is pressed against the surface covered by the pre-treatment composition, and mechanical vibrations are coupled into the element 5, the thermoplastic material of the element at the interface to the pre-treatment composition starts melting and ultimately is welded to the thermoplastic matrix 31. A substantial portion of the curable component may move to the surface. In this, the vibrations are the driving force for the movement of the vesicles 32, and the path of the vesicles may be a random-walk-like path, similar to a path for example known for Brownian-motion of suspended particles in a carrier gas. Because the curable material often does not mix well with the thermoplastic matrix, for energy reasons the vesicles—depending on the material composition—may have the tendency to remain at the interface to the substrate (dentine, tooth enamel, bone, or substitute material). At the surface of the substrate, the curable material may cure and form an attachment to the surface. It further connects to the thermoplastic material surrounding it by chemical bonds and/or by being anchored in it due to the intertwining of the two phases.

In this, the curing may be brought about directly or indirectly (via heat) by the mechanical vibration. In addition or as an alternative, the chemical environment the material meets at the surface may cause the curing or contribute to it. In addition or as yet another alternative, the curing may be initiated during or after the process of coupling mechanical vibration into the system conventionally by heating and/or irradiation (such as UV irradiation and/or waiting). Various curable materials for dental or surgical applications are known in the field, and the curing may appropriately chosen.

In FIG. 6*b*, the cured portions of the curable material are denoted by 32*.

Prior to laying the pre-treatment preparation on the surface, the latter may have been pre-treated, for example by etching and/or by other means, including the application of a primer and/or a starter.

Figure 7:
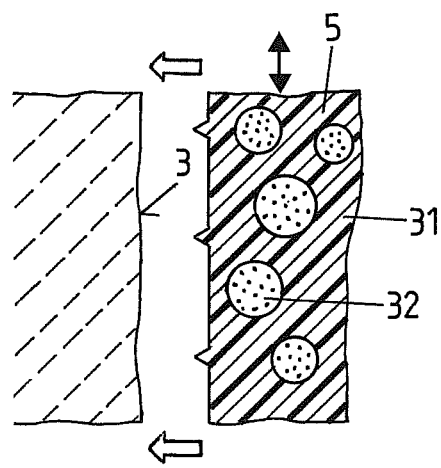
FIG. 7 illustrates yet an other exemplary method according to the invention.

In the variant depicted in FIG. 7, no pre-treatment preparation is applied to the surface. Rather, the attachment composition is a composition of the element 5 or a surface portion thereof. Like in the embodiment of FIGS. 6*a* and 6*b*, after portions of the thermoplastic matrix 31 have melted, the vesicles 32 under the effect of the mechanical vibration may at least in part move to the surface of the element and there be in contact with the surface 3 to which, after curing, they adhere. Again, curing may be brought about during the process of the mechanical vibration (and possibly by the direct or indirect effect of the mechanical vibration) and/or thereafter.

Figure 8:
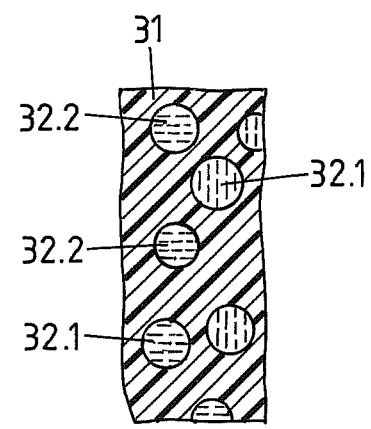
FIG. 8 illustrates a principle of an attachment composition with a hardenable component that has two constituents.

FIG. 8 depicts an attachment composition in which the curable component comprises vesicles of two constituents. A first constituent 32.1 may, for example, be a cross-linkable polymer, or an unpolymerized or partially polymerized composition, and the second constituent 32.2 may then comprise a chemical additive (hardener, polymerization promoter, cross-linking agent) that promotes a hardening of the first constituent. Under the effect of the mechanical vibration and the full or partial liquefaction of the polymer matrix 31, the vesicles of the constituents 32.1, 32.2 will get together and get to the surface, where the hardening occurs. The attachment composition of FIG. 8 may be used in both, a pre-treatment preparation, and/or as the element or portion thereof.

FIGS. 9*a* and 9*b* yet depict, for the example of an embodiment like the one described referring to FIG. 7, the hardening by curing brought about by irradiation, for example by UV radiation 35. The curing process (FIG. 9*b*) takes place after the step of activating by mechanical vibration. Alternatively, it may set in also during the vibration.

FIGS. 10*a* and 10*b* show an embodiment, in which a pre-treatment composition 37 is applied to the surface 3 prior to bringing the attachment composition (of the element to be affixed) in contact with the surface. The pre-treatment composition comprises a material capable of bringing about a curing process together with the hardenable component 32 of the attachment composition. For example, one of the pre-treatment composition 37 and of the hardenable component 32 (present in vesicles embedded in the thermoplastic matrix 31 in the depicted embodiment) may, for example, be a cross-linkable polymer, or an unpolymerized or partially polymerized composition, and the other one may then comprise a chemical additive that promotes a hardening of the former. FIG. 10*b* depicts the hardened composition 38 adhering to the surface 3.

Figure 11A:
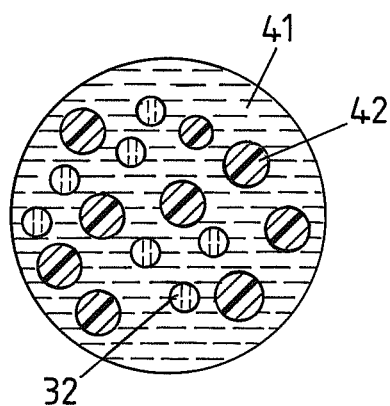
FIG. 11a shows an attachment composition.

FIG. 11*a* depicts a further attachment composition that may, for example, be used for a pre-treatment preparation—applied to the surface in a pasty state—or that may also be used as the material of the element. The composition comprises a carrier liquid 41, in which thermoplastic bodies (particles) 42 and portions (vesicles, bodies) 32 of the curable component are dispersed. The viscosity depends on the concentration and nature of the carrier liquid, as well as on the thermoplastic and curable portions.

Figure 11B:
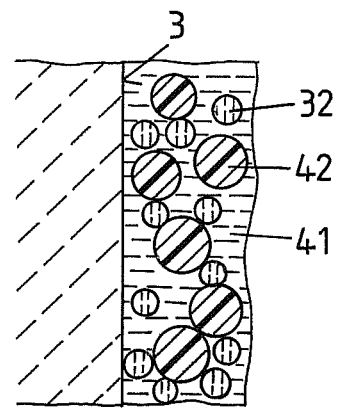
FIG. 11b shows the attachment composition of FIG. 11a applied to a surface.
Figure 11C:
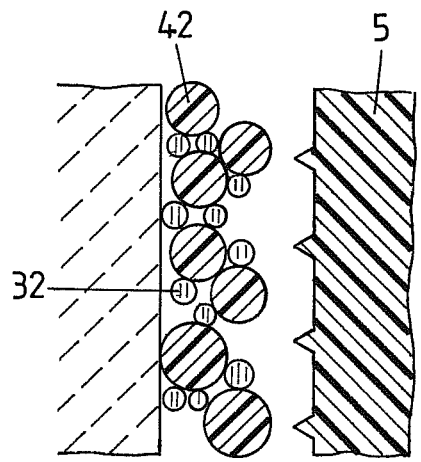
FIG. 11c shows the attachment composition of FIG. 11b after evaporation of the liquid carrier.

The pasty attachment composition may be applied to the surface 3, for example, by a brush applicator, to cover the surface in a thin layer of, for example, less than 200 μm (typically between 20 μm and 100 μm, for example around 50 μm. FIG. 11*b* depicts the layer of the attachment composition applied to the surface 3. Thereafter, the carrier liquid 41 may be removed, for example by letting it evaporate. As shown in FIG. 11*c*, the bodies of the thermoplastic component 42 and the portions of the curable component 31 remain on the surface. When the element 5 to be fastened is pressed against the surface and mechanical vibrations are coupled into the system, the attachment composition is activated. Especially, the following may happen:

the thermoplastic bodies 42 are liquefied and are welded to each other as well as to the thermoplastic material of the element 5.

If the curable component has thermoplastic, thixotropic or viscoelastic properties, the portions of the curable component become more flowable and—assisted by a random movement initiated by the mechanical vibrations, will flow predominantly to the surface 3 and flow together and coat the surface 3 while remaining intertwined with the thermoplastic component.

Depending on the curable component, due to the contact with the (potentially pre-treated) surface and/or due to the heat generated, the curing process of the curable component may start.

Figure 11D:
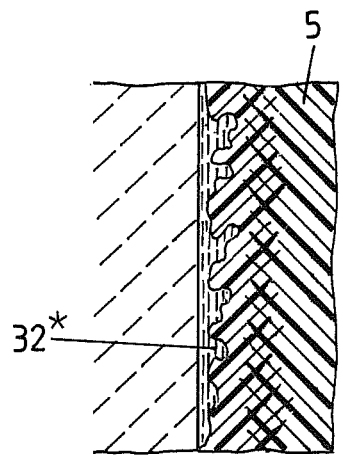
FIG. 11d shows the attachment composition of FIG. 11a after activation.

FIG. 11*d* illustrates the situation after the activation step.

If the curable component is liquid, the process of wetting the surface by the curable component will usually set in already before activation.

If necessary, after the activation step, an additional curing step may be carried out, for example by irradiation, induction, heating for some time, or waiting.

In alternative embodiments, the carrier liquid is not removed prior to the activation step. In these, for example the carrier liquid may to some extent escape during the activation, with the vibrations and heat being the driving force. In addition or as an alternative, the carrier liquid may at least in part remain in the composition and potentially diffuse out and/or be resorbed in time.

In embodiments in which the attachment composition is present in a paste-like (for example 'slurry-like') form, the carrier liquid may optionally be matched with the thermoplastic component so that it is to some extent absorbed by the latter. This may have an effect of making lowering the glass transition temperature of the thermoplastic component, and for example make it softer. Liquefaction of the thermoplastic component then requires less mechanical energy input. This effect and techniques of using it have been described in WO 2008/095 327 incorporated herein by reference in its entirety. If one proceeds in accordance with this option, also the thermoplastic component will be in its final state only after the carrier liquid (solvent) has diffused out and/or is resorbed.

Figure 12A:
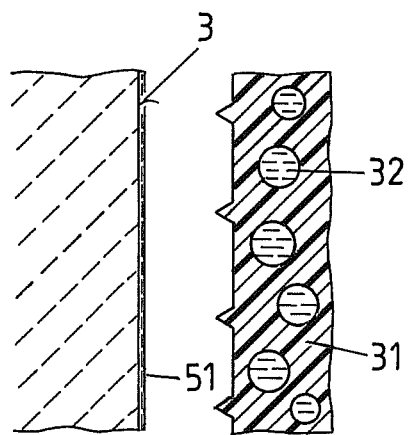
FIG. 12a shows the principle of an even further embodiment of the invention during a first stage.
Figure 12B:
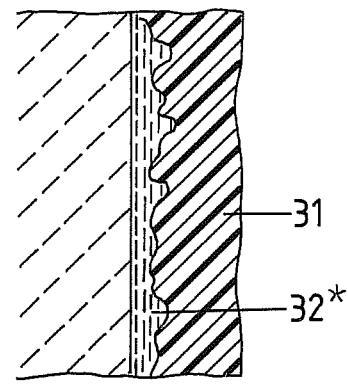
FIG. 12b shows embodiment of FIG. 12a during a second stage.

The embodiment of FIGS. 12*a* and 12*b* is similar to the one of FIGS. 7 and 9*a*/9*b*, with the following additional features:

the surface is, prior to the activation step, pre-treated with a primer 51 that chemically modifies the surface properties. The primer may be applied together with an etchant, or an etchant may have been applied prior to the primer.

The curable component 32 is present in a liquid or liquefiable form and has a tendency to wet the surface 3, so that as an effect of the movement initiated by the mechanical vibration and the liquefaction of the thermoplastic matrix 31, the curable component 32 will coat the surface.

The pre-treatment with a primer 51, while it has been explicitly illustrated only in FIG. 12*a*/12*b*, is an option for all embodiments—and so is the etchant. This pertains to both, these pre-treatment means to be applied individually, together, and/or mixed into the attachment composition, as discussed hereinbefore.

Choosing the curable component so that it has a tendency to wet the surface 3 is an option for all embodiments in which the curable component before curing is sufficiently flowable or is made sufficiently flowable in the activation step due to the effect of the vibrations and/or the heat.

In yet another embodiment, the hardenable component may—similarly to the embodiments of FIGS. 6, 7, 9, 10, 12—be embedded in a thermoplastic matrix, however not as vesicles but molecularly. In a variant of the embodiment of FIGS. 11*a*-11*d*, the curable component may be embedded molecularly (i.e. solved) in the carrier liquid 41 and/or in the thermoplastic bodies 42.

EXAMPLE

In teeth of pigs' carcasses a cavity (without recess) was created or the crown was removed to free the entrance to the root canal. A pre-treatment preparation was applied to the dentine and enamel surfaces of the cavities and root canals, which preparation had been produced by mixing a dental primer preparation on a methacrylate-basis (commercially available for use in conjunction with composite materials on a methacrylate-basis for filling dental cavities) and powdered polyamide. The pre-treatment preparation was cured in situ by UV light. Polyamide elements were then positioned in the pre-treated cavities and root canals and impinged with mechanical oscillation by means of a hand-held ultrasonic device.

In preliminary tests the force required to extract the polyamide elements were ranged around 15 N per $mm^2$ of bonding surface, which was between twice and four times more force than was necessary for the extraction of identical elements from identical cavities and root canals pre-treated with a preparation that did not contain any powdered polyamide.

The invention claimed is:

1. A medical method of affixing an element to a surface, wherein the surface is a surface of dentine, tooth enamel, bone tissue, or corresponding substitute material, the method comprising the steps of:

providing an attachment composition, the attachment composition comprising a mixture of:
a thermoplastic component; and
a hardenable component, the hardenable component being different from the thermoplastic component and being hardenable by cross-linking;
positioning the attachment composition relative to the surface of dentine, tooth enamel, bone tissue, or corresponding substitute material; and
activating the attachment composition to attach the attachment composition to the surface and to the element positioned relative the surface;
wherein the step of activating the attachment composition comprises activating the attachment composition via mechanical vibration,
wherein, subsequent to the step of activating, the element is affixed to the surface by the attachment composition, with the hardenable component being intertwined with and thereby mechanically connected to the thermoplastic component,
wherein the steps of providing and positioning are carried out prior to the step of activating, and
wherein the attachment composition provides a reversible attachment of the element to the surface, the attachment being releasable by causing energy to impinge upon the element until the thermoplastic component is liquefied.

2. The method according to claim 1, wherein the element comprises a first thermoplastic material, wherein the attachment composition is applied as a pre-treatment preparation to the surface prior to the step of positioning, wherein the thermoplastic component of the attachment composition comprises solid bodies of a second thermoplastic material, the first thermoplastic material and the second thermoplastic material being of a same or different composition, and wherein during the step of activating, the first thermoplastic material is welded to the second thermoplastic material.

3. The method according to claim 1, wherein during the step of activating, the hardenable component is at least partly hardened.

4. The method according to claim 1, wherein the hardenable component is provided as portions embedded in a matrix of the thermoplastic component, wherein in the step of activating, the liquefaction of the thermoplastic component is caused by the mechanical vibration, and wherein the mechanical vibration further cause a movement of the portions in the thermoplastic matrix.

5. The method according to claim 4, wherein the portions of the hardenable component are liquid.

6. The method according to claim 4, wherein the portions of the hardenable component have thermoplastic, thixotropic and/or viscoelastic properties, and wherein by the step of activating, the flowability of the hardenable component is enhanced.

7. The method according to claim 4, wherein in the step of activating a substantial percentage of the portions propagates to the surface and wets the surface.

8. The method according to claim 1, wherein the attachment composition further comprises a carrier liquid, in which the thermoplastic component and the hardenable component are at least one of dissolved and of dispersed.

9. The method according to claim 1, wherein the hardenable component is a curable component or a constituent of a curable component.

10. The method according to claim 1, wherein the attachment composition is a composition of a pre-treatment preparation applied to the surface prior to the positioning of the element relative to the surface.

11. The method according to claim 1, wherein the attachment composition is a composition of the element.

12. The method according to claim 11, wherein the attachment composition is a composition of a surface portion of the element.

13. The method according to claim 11, wherein the attachment composition is a composition of the entire element.

14. The method according to claim 1, wherein the step of activating comprises causing mechanical vibration to impinge on the element while the element is pressed against the surface.

15. The method according to claim 1, wherein the mechanical vibration has a frequency of 2 to 200 kHz.

16. The method according to claim 1, wherein the element to be affixed is one of: a dental filling, a dental inlay, a dental veneer, a root pin, a piece of jewelry to be attached to a tooth, a dental bracket, a dental crown, a dental bridge, an implant to be implanted in bone tissue, an endoprosthesis, and an element with a therapeutic function to be attached to a bone.

17. The method according to claim 1, wherein the step of activating comprises causing the mechanical vibration to impinge on the attachment composition until the thermoplastic component is liquefied.

18. The method according to claim 1, comprising the further step of causing the hardenable component to harden after the step of activating.

19. The medical method according to claim 9,
wherein the hardenable component is dissolved or dispersed in the attachment composition,
wherein portions of the curable component are caused to be released to the surface and to coat the surface at least partially prior to the step of activating or during the step of activating or prior to and during the step of activating; and
wherein the steps of providing and positioning are carried out prior to the activating step.

20. An attachment composition for affixing an element to a surface, the surface being a surface of dentine, tooth enamel, bone tissue, or corresponding substitute material, the attachment composition comprising a mixture of:
a thermoplastic component;
a hardenable component, the hardenable component being different from the thermoplastic component and being hardenable by cross-linking; and
a carrier liquid;
wherein the thermoplastic component and the hardenable component are mixed prior to being applied to the surface,
wherein the thermoplastic component and the hardenable component are at least one of dissolved and dispersed in the carrier liquid, and
wherein at least one of the components is activatable by mechanical vibrations impinging on the attachment composition such that, subsequent to being activated, the element is affixed to the surface by the attachment composition, with the hardenable component being intertwined with and thereby mechanically connected to the thermoplastic component.

21. A set for affixing an element to a surface, the surface being a surface of dentine, tooth enamel, bone tissue, or corresponding substitute material, the set comprising:
the element to be affixed;
an attachment composition according to claim 20; and information on the mixture of thermoplastic component and hardenable component to form the attachment composition and on use of mechanical vibration for affixing the element to the surface;

wherein the information teaches the use of the mechanical vibration to activate the attachment composition, which has previously been applied between the element and surface, to thereby affix the element to the surface with the hardenable component being intertwined with and thereby mechanically connected to the thermoplastic component.

22. A medical method of affixing an element to a surface, wherein the surface is a surface of dentine, tooth enamel, bone tissue, or corresponding substitute material, the method comprising the steps of:

providing an attachment composition, the attachment composition comprising a mixture of:
 a thermoplastic component; and
 a hardenable component, the hardenable component being different from the thermoplastic component and being hardenable by cross-linking;
positioning the attachment composition relative to the surface of dentine, tooth enamel, bone tissue, or corresponding substitute material; and
activating the attachment composition to attach the attachment composition to the surface and to the element positioned relative the surface;
wherein the step of activating the attachment composition comprises activating the attachment composition via mechanical vibration,
wherein, subsequent to the step of activating, the element is affixed to the surface by the attachment composition, with the hardenable component being intertwined with and thereby mechanically connected to the thermoplastic component,
wherein the steps of providing and positioning are carried out prior to the step of activating; and wherein the element comprises a first thermoplastic material,
wherein the thermoplastic component of the attachment composition comprises solid bodies of a second thermoplastic material, the first thermoplastic material and the second thermoplastic material being of a same or different composition, and
wherein during the step of activating, the first thermoplastic material is welded to the second thermoplastic material.

23. The method according to claim 22, comprising the further step of:
after applying the pre-treatment preparation, hardening the hardenable component;
wherein the steps of applying and of hardening are carried out prior to the step of activating.

24. A medical method of affixing an element to a surface, wherein the surface is a surface of dentine, tooth enamel, bone tissue, or corresponding substitute material, the method comprising the steps of:

providing an attachment composition, the attachment composition comprising a mixture of:
 a thermoplastic component; and
 a hardenable component, the hardenable component being different from the thermoplastic component and being hardenable by cross-linking;
positioning the attachment composition relative to the surface of dentine, tooth enamel, bone tissue, or corresponding substitute material; and
activating the attachment composition to attach the attachment composition to the surface and to the element positioned relative the surface;
wherein the step of activating the attachment composition comprises activating the attachment composition via mechanical vibration,
wherein, subsequent to the step of activating, the element is affixed to the surface by the attachment composition, with the hardenable component being intertwined with and thereby mechanically connected to the thermoplastic component,
wherein the steps of providing and positioning are carried out prior to the step of activating, and
wherein during the step of activating, the hardenable component is at least partly hardened.

25. The method according to claim 24, wherein the hardenable component is capable of hardening thermally, and wherein during the step of activating, the hardenable component is at least partly hardened due to the effect of absorbed mechanical energy turned into heat.

26. The method according to claim 24, wherein the hardenable component is hardenable by bringing together a first and a second constituent, and wherein in the step of activating, the first and second constituents are brought together.

27. The method according to claim 26, wherein the hardenable component comprises the first constituent and the second constituent, the first and second constituents being embedded in the thermoplastic component and being separate from each other, and wherein in the step of activating, the thermoplastic component is liquefied and the hardening occurs by the bringing together of the first and second constituents made possible by the liquefaction.

28. The method according to claim 26, wherein the hardenable component comprises one of the first and second constituents, and wherein the method comprises the step of applying a pre-treatment composition comprising an other one of the constituents to the surface prior to the step of bringing the attachment composition in contact with the surface.

29. A medical method of affixing an element to a surface, wherein the surface is a surface of dentine, tooth enamel, bone tissue, or corresponding substitute material, the method comprising the steps of:

providing an attachment composition, the attachment composition comprising a mixture of:
 a thermoplastic component; and
 a hardenable component, the hardenable component being different from the thermoplastic component and being hardenable by cross-linking;
positioning the attachment composition relative to the surface of dentine, tooth enamel, bone tissue, or corresponding substitute material; and
activating the attachment composition to attach the attachment composition to the surface and to the element positioned relative the surface;
wherein the step of activating the attachment composition comprises activating the attachment composition via mechanical vibration,
wherein, subsequent to the step of activating, the element is affixed to the surface by the attachment composition, with the hardenable component being intertwined with and thereby mechanically connected to the thermoplastic component,
wherein the steps of providing and positioning are carried out prior to the step of activating, and wherein the attachment composition further comprises a carrier liquid, in which the thermoplastic component and the hardenable component are at least one of dissolved and of dispersed.

30. The method according to claim 29, wherein the attachment composition, prior to the step of activating, is liquid or paste-like and wherein the step of positioning comprises applying the attachment composition onto the surface.

31. The method according to claim 29, further comprising the step of causing at least a portion of the carrier liquid to be removed after the step of positioning and prior to the step of activating.

32. The method according to claim 29, wherein the hardenable component comprises portions suspended in the carrier liquid.

33. The method according to claim 32, wherein the portions are solid bodies.

34. The method according to claim 33, wherein the portions have thermoplastic, thixotropic and/or viscoelastic properties, and wherein by the step of activating, the flowability of the hardenable component is enhanced.

35. A medical method of affixing an element to a surface, wherein the surface is a surface of dentine, tooth enamel, bone tissue, or corresponding substitute material, the method comprising the steps of:
providing an attachment composition, the attachment composition comprising a mixture of:
a thermoplastic component; and
a hardenable component, the hardenable component being different from the thermoplastic component and being hardenable by cross-linking;
positioning the attachment composition relative to the surface of dentine, tooth enamel, bone tissue, or corresponding substitute material; and
activating the attachment composition to attach the attachment composition to the surface and to the element positioned relative the surface;
wherein the step of activating the attachment composition comprises activating the attachment composition via mechanical vibration,
wherein, subsequent to the step of activating, the element is affixed to the surface by the attachment composition, with the hardenable component being intertwined with and thereby mechanically connected to the thermoplastic component,
wherein the steps of providing and positioning are carried out prior to the step of activating, and
wherein the step of activating causes mechanical vibration to impinge on the element while the element is pressed against the surface.

36. The method according to claim 35 wherein the mechanical vibration is coupled into the element by means of a sonotrode.

* * * * *